United States Patent [19]

Yuki et al.

[11] Patent Number: 4,619,984

[45] Date of Patent: Oct. 28, 1986

[54] PACKING FOR USE IN RESOLUTION

[75] Inventors: Yoichi Yuki; Akito Ichida, both of Himeji, Japan

[73] Assignee: Daicel Chemical Industries, Ltd., Sakai, Japan

[21] Appl. No.: 717,267

[22] PCT Filed: Jul. 20, 1984

[86] PCT No.: PCT/JP84/00369

§ 371 Date: Mar. 15, 1985

§ 102(e) Date: Mar. 15, 1985

[87] PCT Pub. No.: WO85/00661

PCT Pub. Date: Feb. 14, 1985

[30] Foreign Application Priority Data

Jul. 20, 1983 [JP] Japan ............................... 58-132361
Aug. 19, 1983 [JP] Japan ............................... 58-150383
Aug. 26, 1983 [JP] Japan ............................... 58-154993

[51] Int. Cl.$^4$ ............................................. C08G 77/26
[52] U.S. Cl. .................................... 528/38; 528/10; 528/39; 252/184; 252/190; 252/315.6; 210/502.1; 210/510.1

[58] Field of Search ............................ 210/502.1, 510.1; 252/184, 190, 315.6; 528/38, 10, 39

[56] References Cited

U.S. PATENT DOCUMENTS

| | | | |
|---|---|---|---|
| 4,029,583 | 6/1977 | Chang et al. | 252/184 |
| 4,322,310 | 3/1982 | House | 252/184 |
| 4,324,681 | 4/1982 | House | 252/184 |
| 4,455,415 | 6/1984 | Panster et al. | 528/39 |
| 4,522,724 | 6/1985 | Ramsden | 210/502.1 |

*Primary Examiner*—Melvyn I. Marquis
*Attorney, Agent, or Firm*—Flynn, Thiel, Boutell & Tanis

[57] ABSTRACT

A packing for use in resolution proposed for the liquid chromatography particularly for the optical resolution of racemic compounds is prepared by reacting a silica gel carrier with a so-called silane treating agent to introduce a spacer part therein and chemically bonding it with a copper salt of a carboxylic or thiocarboxylic acid selected from the group consisting of optically active D- and L-2-acetizinecaroxylic acid, proline, hydroxyproline and allohydroxyproline. The steric bulkiness, the distance between the silica gel and the optically active group and the degree of hydrophobicity are specified so as to obtain an excellent resolving power.

18 Claims, No Drawings

PACKING FOR USE IN RESOLUTION

DESCRIPTION

1. Technical Field

The present invention relates to a new packing for use in resolution, particularly in liquid chromatography for optical resolution of racemic compounds. The packing proposed by the present invention is prepared by reacting a silica gel carrier with a so-called silane treating agent to introduce a spacer part therein and chemically bonding it with an optically active D- or L-group.

2. Background Art

Packings for use in optical resolution, comprising silica gel chemically bonded with optically active proline or hydroxyproline, have a carboxyl group coordination-bonded or ionically bonded with a copper ion as described in G. Gübitz et al. "J. High Resolut. Chromatogr. and Chromatogr. Comm." 2, 145 (1979), K. Sugden et al. "J. Chromatogr." 192, 228 (1980) and V. A. Davankov et al. "Angew. Chem. Int. Ed. Engl." 21, 930 (1982). These packings resolve racemic compounds by taking advantage of a difference in the free energy of the mutual action of the respective antipodes of amino acids with the coordinatable racemic compounds.

In using the conventional packings for resolution, the optically active amino group is bonded with the silane treating agent which acts as the spacer and, therefore, the spacer exerts a significant influence on the resolving capacity and synthetic techniques have been greatly restricted in designing such packings. As described by V. A. Davankov et al. in "Chromatographia" 13, 677 (1980), a process wherein L-hydroxyproline containing a straight-chain alkyl group having 7 to 16 carbon atoms is adsorbed on a reversed phase silica gel column to effect the optical resolution has problems that the groups to be introduced into the amino group are limited to hydrophobic groups and the reactivity and the selection of solvent are difficult. Similar optical resolution packings are disclosed in the specifications of Japanese Patent Laid-Open No. 96062/1983 and corresponding West German Patent Laid-Open No. 3,143,726.

After intensive investigations made for the purpose of further improving the capacities of the known packings, the inventors have found that the resolving power is greatly influenced by the steric bulkiness of the silane treating agent, the distance between the silica gel and the optically active group and the degree of hydrophobicity in said resolution mechanism. The present invention has been completed on the basis of these findings.

DISCLOSURE OF INVENTION The present invention provides a packing for use in resolution comprising a substance of the following general formula (I):

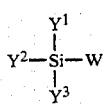

(I)

wherein at least one of $Y^1$, $Y^2$ and $Y^3$ represents a silica gel and siloxane bond with the silica gel and the balance represents a hydrogen atom, an alkyl group having 1 to 20 carbon atoms, an aryl group having 6 to 20 carbon atoms, an aralkyl group having 7 to 20 carbon atoms, a halogen atom, a hydroxy group, an alkoxy group having 1 to 20 carbon atoms or any desired combination of them, and W represents (1) $-X-R$ (2) 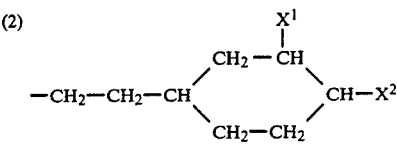

(3) $-X-R^1$ or (4) $-X-R^2$, in which X represents a spacer having 1 to 30 carbon atoms, R represents an optically active group of the general formula:

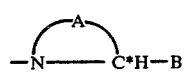

where A is a substituted or unsubstituted alkylene group having 2 or 3 carbon atoms and B is a metal thiocarboxylate group, one of $X^1$ and $X^2$ represents a hydroxy group and the other represents an optically active group of the formula:

where $B^1$ is a metal carboxylate group, $R^1$ represents an optically active group of the general formula:

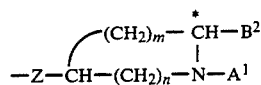

where m and n are each 0 or an integer of 1 to 3 and the total of these numbers is up to 3, $B^2$ is a copper carboxylate or thiocarboxylate, Z is an oxygen atom, a sulfur atom or an amino group and $A^1$ is a hydrogen atom, an alkyl group having 1 to 40 carbon atoms, an aryl group having 6 to 40 carbon atoms, an aralkyl group having 7 to 47 carbon atoms or a group having 1 to 40 carbon atoms and a hetero atom, e.g., a group having an ether, amino, thioether, amide, ester, sulfonate or urethane bond, and $R^2$ represents an optically active group of the general formula:

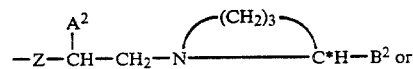

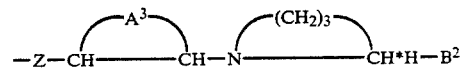

where $A^2$ is a hydrogen atom, an alkyl group having 1 to 40 carbon atoms, an aryl group having 6 to 40 carbon atoms, an aralkyl group having 7 to 47 carbon atoms or a group having 1 to 40 carbon atoms and a hetero atom, i.e., a group having an ether, amino, thioether, amide or ester bond, $A^3$ is methylene having 2 to 6 carbon atoms and * designates an asymmetric carbon atom.

The packing of the present invention serves to reduce the time required for effecting chromatography remarkably as compared with that of the conventional processes without damaging the resolving power. Further, the flow rate of the solvent necessitated in the chromatography can be reduced remarkably and, therefore, the pressure applied to the packing can be reduced and deterioration of the column due to crushing of silica gel can be reduced significantly.

The resolution packing of the present invention is packed in a metal or glass cylinder in an ordinary liquid chromatograph for use in an optical resolution of racemic compounds.

The packing of the present invention as defined by the above general formula (I) may be classified into four groups with respect to W in this formula. The present invention will be illustrated further with reference to the classification.

The packing (1) of the present invention can shorten the time required for the chromatography remarkably as compared with that of the conventional processes without deterioration of the resolving power. Further, the flow rate of the solvent necessitated in chromatography can be reduced remarkably and, therefore, the pressure applied to the packing can be reduced and deterioration of the column due to the crushing of silica gel can be reduced significantly.

The inventors have found that when the carboxyl group of the conventional packing is replaced with a thiocarboxyl group, its bonding power with copper ion is increased and the packing is stabilized while the mutual action thereof with racemic compounds is weakened relatively. The resolution packing (1) of the present invention has been completed on the basis of this finding.

A resolution packing (2) proposed in the present invention is obtained by chemically modifying silica gel by reacting it with a silane treating agent, i.e. [2-(7-oxabicyclo-[4.1.0]hept-3-yl)ethylene]silane and chemically bonding this product with any of copper salts of optically active D- or L-2-azetidinecarboxylic acid, proline, hydroxyproline and allohydroxyproline.

The inventors have found that when [2-(7-oxabicyclo-4.1.0]hept-3-yl)ethyl]silane is used as the silane treating agent, the steric control of the fixed optically active ligand and an increase in the hydrophobicity are simultaneously realized to improve the resolving power far more remarkably than that obtained by using the conventional resolving agent. The resolution packing (2) of the present invention has been developed on the basis of this finding.

The resolution packing (3) proposed by the present invention is obtained by reacting a silica gel carrier with a so-called silane treating agent to introduce a spacer part therein and chemically bonding the product with a copper salt of a carboxylic or thiocarboxylic acid selected from the group consisting of optically active D- and L-azetidinecarboxylic acid, proline, hydroxyproline and allohydroxyproline.

Any desired group can be introduced into the amino group of the resolution packing agent (3) of the present invention and, therefore, the active center of the optical resolution can be designed as desired. Further, the silane treating agent which acts as the spacer is reacted with a reacting point exerting substantially no influence on the active center such as hydroxy group to avoid the influence of the silane treating agent. As a result, the product (3) has a resolution power far higher than that of the conventional resolution packing.

The resolution packing (4) proposed by the present invention is obtained by reacting a silica gel carrier with a so-called silane treating agent to introduce a spacer part therein and chemically bonding the product with a copper salt of an optically active D- or L-proline or a corresponding thiocarboxylic acid.

Any desired group can be introduced into the amino group according to the present invention and, therefore, the active center of the optical resolution can be designed as desired. Further, by reacting the silane treating agent which acts as the spacer with a group which exerts substantially no influence on the active center such as a hydroxy, thiol or amino group to form a bond, the influence of the silane treating agent can be eliminated. As a result, the product (4) has a resolution power far higher than that of the conventional resolution packing agent.

The resolution packing of the present invention comprising the substance of the above general formula (I) comprises the silica gel (A) bonded with the optically active group (C) through the silane treating agent (B). The respective components of the packing will now be illustrated.

(A) Silica gel:

The starting silica gel has a particle diameter of 0.1 to 1000 μm and a pore diameter of 10 to 10,000 Å, preferably a particle diameter of 1 to 100 μm and a pore diameter of 50 to 5,000 Å.

Now, the description will be made of the silane treating agent used for forming the packing of the general formula I-(1) and the optically active group.

(B) Silane treating agent:

Any of known silane treating agents may be used as the silane treating agent in forming the spacer part of the packing I-(1) of the present invention. They are represented by the following formula (II)-(1):

wherein Y, Y' and Y" represent each a hydrogen atom, an alkyl group having 1 to 20 carbon atoms, an aryl group having 6 to 20 carbon atoms, an aralkyl group having 7 to 20 carbon atoms, a halogen atom, a hydroxy group, an alkoxy group having 1 to 20 carbon atoms or any combination thereof with the proviso that, after the silane treating agent has reacted with the silica gel, Y, Y' and Y" remaining unreacted with the silica gel coincide with $Y^1$, $Y^2$ and $Y^3$ of the above formula (I) remaining unreacted with the silica gel.

X' represents a spacer-forming group having 1 to 30 carbon atoms, i.e. an alkyl or aryl group having a halogen atom, an amino group or an oxirane group at a terminal or inside thereof and it may contain a hetero atom. Namely, it may have any desired bond such as ether, ester, amino or amide bonds. Therefore, the radical X in the general formula (I)-(1) is a residue obtained after X' of the general formula (II)-(1) is reacted with R.

More specifically, the silane treating agents of the general formula (II)-(1) are those having a functional group reactive with the secondary amino group to form a covalent bond. Examples of these agents include the following compounds:

(1) compounds of the above formula wherein X' represents —CH₂Cl or —CH₂Br:
chloromethyldimethylchlorosilane
chloromethyldimethylethoxysilane,
bromomethyldimethylchlorosilane,
chloromethylmethyldichlorosilane,
chloromethylmethyldiethoxysilane,
chloromethyltrichlorosilane,
chloromethyltriethoxysilane,
chloromethyldimethyl- -nitrophenoxysilane,
chloromethyldimethyl-p-nitrophenoxysilane,
chloromethyldimethyl-2- [(2-ethoxyethoxy)ethoxy]silane,
chloromethyldimethylphenoxysilane,
1,2-bis(dimethylchlorosilyl)ethane, and
allyloxychloromethyldimethylsilane, (2) compounds of the above formula wherein X' represents —CH₂CH₂CH₂Cl or —CH₂CH₂CH₂Br:
3-chloropropyltrimethoxysilane,
3-chloropropyldimethoxymethylsilane,
3-chloropropylmethyldichlorosilane,
3-chloropropyltrichlorosilane,
3-bromopropyldimethylchlorosilane,
3-bromopropyltrichlorosilane,
3-bromopropyltrimethoxysilane,
3-chloropropyldimethylchlorosilane,
3-chloropropylmethyldimethoxysilane,
3-chloropropyltriethoxysilane,
3-chloropropylphenyldichlorosilane, and
n-propyl(3-chloropropyl)dichlorosilane, (3) compounds of the above formula wherein X' represents

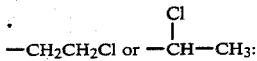

1-chloroethylmethyldichlorosilane,
2-chloroethylmethyldichlorosilane,
1-chloroethyltrichlorosilane, and
2-chloroethyltrichlorosilane, (4) compounds of the above formula wherein X' represents

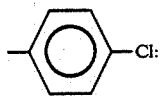

p-chlorophenyltrimethoxysilane, and
p-chlorophenyltriethoxysilane, (5) compounds of the above formula wherein X' represents

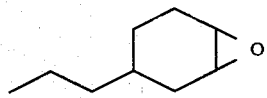

2-(3,4-epoxycyclohexylethyl)trimethoxysilane, (6) compounds of the above formula wherein X' represents

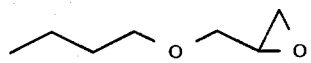

3-glycidoxypropyltrimethoxysilane,
diethoxy-3-glycidoxypropylmethylsilane, and
3-glycidoxypropyldimethylethoxysilane, (7) compounds of the above formula wherein X' represents a halogenoalkyl:
8-bromooctyltrichlorosilane, and
4-(methyldichlorosilyl)butyl chloride, (8) compounds of the above formula wherein X' represents an acid chloride:
2-(4-chlorosulfonylphenyl)ethyltrichlorosilane,
2-(4-chlorosulfonylphenyl)ethyltrimethoxysilane, and
3-(trichlorosilyl)propyl chloroformate.

(C) Optically active group:

The optically active group R constituting the characteristic part of the packing I-(1) of the present invention is represented by the following general formula (III)-(1):

wherein A represents an unsubstituted or substituted alkylene group having 2 or 3 carbon atoms, B represents a metal thiocarboxylate group, and * refers to an asymmetric carbon atom.

More specifically, a D- or L-compound selected from the group consisting of optically active 2-azetidinecarboxylic acid, proline, hydroxyproline and allohydroxyproline is used. Generally, easily available L-compounds are used. The thiocarboxylic acid is converted into its metal salt by reacting its alkyl, aryl or aralkyl ester with a metal salt of hydrogen sulfide such as sodium hydrosulfide or potassium hydrosulfide in an anhydrous solvent. The conversion may be effected also by a process disclosed in I. Shahak et al. "J. Am. Chem. Soc." 95, 3440 (1973)

Now, a description will be made of the silane treating agent and the optically active group of the packing I-(2) of the present invention.

(B) Silane treating agent:

The silane treating agent constituting the characteristic part of the packing of the present invention is represented by the following general formula (II)-(2):

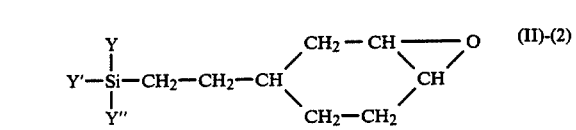

wherein Y, Y' and Y" have the same meaning as in the above formula (II)-(1) with the proviso that at least one of them represents a halogen atom, a hydroxy group or an alkoxy group having 1 to 20 carbon atoms.

(C) Optically active group:

The optically active group R forming the characteristic part of the packing of the present invention is represented by the following general formula (III)-(2)

wherein A has the same meaning as in the formula (III)-(1), B¹ represents a metal carboxylate group, and * refers to an asymmetric carbon atom.

More specifically, a D- or L-compound selected from the group consisting of optically active 2-azetidinecarboxylic acid, proline, hydroxyproline and allohydroxyproline is used. Generally, easily available L-compounds are used.

The packing (I)-(3) will now be illustrated.

(B) The silane treating agent used is the same as that used in (I)-(1).

(C) Optically active group:

The optically active group $R^1$ constituting the characteristic part of the packing (I)-(3) of the present invention is represented by the following general formula (III)-(3):

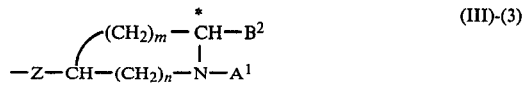

$$-Z-\overset{*}{C}H-(CH_2)_n-N-A^1 \quad \text{(III)-(3)}$$
(with branch $(CH_2)_m-CH-B^2$)

wherein m and n each represents 0 or an integer of 1 to 3, the total of m and n being up to 3, $B^2$ represents a copper carboxylate or thiocarboxylate, Z represents an oxygen atom, a sulfur atom or an amino group, $A^1$ represents a hydrogen atom, an alkyl group having 1 to 40 carbon atoms, an aryl group having 6 to 40 carbon atoms, an aralkyl group having 7 to 47 carbon atoms or a group having 1 to 40 carbon atoms and a hetero atom, i.e. a group having a bond selected from the group consisting of ether, amino, thioether amide, ester, sulfonate and urethane bonds and * refers to an asymmetric carbon atom.

More specifically, it is obtained by introducing the above-mentioned substituent $A^1$ into the secondary amino group of starting, optically active D- or L-hydroxyproline or allohydroxyproline to convert said secondary group into a tertiary group. It is necessary in this case that the hydroxy group of the proline skeleton is selectively reacted with the silane treating agent to form a bond.

Examples of the substituent $A^1$ include straight-chain and branched hydrocarbon groups such as methyl, ethyl, propyl, isopropyl, butyl, tert-butyl, octyl, decyl, dodecyl, hexadecyl, octadecyl and eicosyl groups; cyclic hydrocarbon groups such as cyclopentyl and cyclohexyl groups; aromatic hydrocarbon groups such as phenyl and benzyl groups and groups containing these aromatic hydrocarbon groups; heterocyclic groups such as pyridyl and imidazolyl groups and groups containing them; hetero atom-containing cyclic or acyclic hydrocarbon groups such as methoxyethyl, methylthioethyl, N-morpholylethyl and N,N-dimethylaminoethyl groups; as well as carboxymethyl, p-toluenesulfonyl, carbo-benzyloxy, benzoyl and tert-butoxycarbonyl groups.

The description will be made on the packing (I)-(4).

(B) The silane treating agent used is the same as that used in (I)-(1).

(C) Optically active group:

The optically active group $R^2$ constituting the characteristc part of the packing of the present invention is represented by the following general formula:

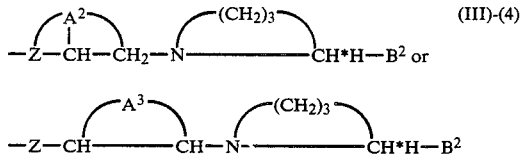

$$-Z-CH-CH_2-N\overset{A^2}{\underset{}{\diagup}}\diagdown \overset{(CH_2)_3}{\underset{}{\diagup}}\diagdown CH^*H-B^2 \text{ or}$$

$$-Z-CH\overset{A^3}{\underset{}{\diagup}}\diagdown CH-N\overset{(CH_2)_3}{\underset{}{\diagup}}\diagdown CH^*H-B^2 \quad \text{(III)-(4)}$$

wherein $B^2$ represents a copper carboxylate or thiocarboxylate group, Z represents an oxygen atom, a sulfur atom or an amino group, $A^2$ represents a hydrogen atom, an alkyl group having 1 to 40 carbon atoms, an aryl group having 6 to 40 carbon atoms, an aralkyl group having 7 to 47 carbon atoms or a group having 1 to 40 carbon atoms and a hetero atom, i.e. a group having a bond selected form the group consisting of ether, amino, ethioether, amide and ester bonds, $A^3$ represents a methylene group having 2 to 6 carbon atoms and * refers to an asymmetric carbon atom.

Specifically, said compound is obtained by introducing the above-mentioned substituent $A^2$ into the secondary amino group of the starting, optically active D- or L-proline to convert said group into a tertiary group.

More particularly, said compound is obtained by the ring-opening addition reaction of said proline with an α-olefin epoxide or cyclic epoxide.

Examples of the substituent $A^2$ include straightchain and branched hydrocarbon groups such as methyl, ethyl, propyl, isopropyl, butyl, tert-butyl, octyl, decyl, dodecyl, hexadecyl, octadecyl and eicosyl groups; cyclic hydrocarbon groups such as cyclopentyl and cyclohexyl groups; aromatic hydrocarbon groups such as phenyl and benzyl groups and groups containing these aromatic hydrocarbon groups; heterocyclic groups such as pyridyl and imidazolyl groups and groups containing them; and hetero atom-containing cyclic or acyclic hydrocarbon groups such as methoxyethyl, methylthioethyl, N-morpholylethyl and N,N-dimethylaminoethyl groups.

The resolving agent of the present invention may be prepared from the above-mentioned starting materials (A), (B) and (C) by treating silica gel with silane and then bonding the silica gel with the optically active group or by previously bonding the silane treating agent with the optically active group and then reacting the resulting product with the silica gel. The reaction for the conversion of the carboxyl group or its ester into the metal thiocarboxylate may be conducted either before or after the bonding with the silica gel. The metal salt may be converted into a corresponding copper salt by exchange reaction with a copper salt of a strong acid.

As described above, the resolution packing of the present invention comprises the silica gel chemically bonded with the optically active group through the silane treating agent. The resolution packing is suitable for use as a liquid chromatographic packing particularly for the optical resolution of amino acids.

The following synthesis examples of the resolution packings of the present invention, examples thereof and comparative examples will further illustrate the present invention, which by no means limit the invention.

SYNTHESIS EXAMPLE 1

Silica gel was dried by heating to 120° to 150° C. in a dry nitrogen stream for 2 to 10 h. 20 g of the dry silica gel was suspended in 100 ml of anhydrous benzene. 6 g of glycidoxypropyltrimethoxysilane was added to the suspension and the mixture was heated under reflux in a dry nitrogen stream. The reaction was carried out for 5 to 10 h while methanol thus formed was removed from the reaction system. After completion of the reaction, the mixture was cooled to room temperature and filtered through a glass filter. The resulting modified silica gel was washed with anhydrous benzene and dried at 40° C. in a vacuum. 4.1 g (0.02 mol) of L-proline benzyl ester was dissolved in 250 ml of anhydrous dimethylformamide. 20 g of the silica gel having glycidoxypropylsilyl group was added to the above obtained solution to obtain a suspension, which was then agitated at 90° C. for 4 h. The suspension was cooled to room temperature. A solution of 1.2 g (0.021 mol) of sodium hydrosulfide in methanol was added to the suspension and the mixture was agitated at room temperature for 19 h to replace the benzyl ester group with sodium thiocarboxylate. The obtained, modified silica gel was filtered, washed with methanol and poured into a solution of 6 g of copper sulfate in 50 ml of pure water to obtain a copper salt. The copper salt was filtered and washed with pure water to obtain a silica gel chemically bonded with the copper salt of L-2-pyrrolidinecarbothioic acid.

The structural formula of this product was estimated to be as follows:

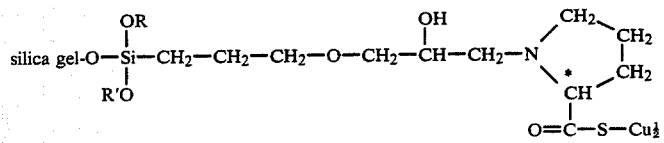

wherein one or both of R and R' represent a methyl group or both or either of them is the same silica gel as above.

EXAMPLE 1

Various racemic amino acids were optically resolved with the packing obtained in Synthesis Example 1. The packing obtained from wholly porous silica gel having an average particle diameter of 10 μm and an average pore diameter of 100 Å in the above Synthesis Example 1 was placed in a stainless steel high-performance liquid chromatographic column (25 cm×0.46 cm). Racemic amino acids were optically resolved at a flow rate of 2 ml/min at 50° C. using a 5×10$^{-4}$M aqueous copper nitrate solution as the solvent to obtain excellent resolution effects as shown in Table 1. The pressure applied to the packing was 30 kg/cm$^2$G.

TABLE 1

| Amino acid | Capacity factor $k'_L$ | Capacity factor $k''_D$ | Separation factor ($\alpha$) | Resolution factor (Rs) |
|---|---|---|---|---|
| threonine | 1.71 | 1.18 | 1.45 | 1.4 |
| serine | 1.61 | 1.00 | 1.61 | 1.6 |
| proline | 1.29 | 2.04 | 1.58 | 2.0 |
| histidine | 3.57 | 2.36 | 1.52 | 2.4 |
| isoleucine | 2.14 | 1.43 | 1.50 | 2.2 |
| methionine | 1.93 | 1.68 | 1.15 | 0.8 |
| lysine | 2.79 | 2.39 | 1.16 | — |
| ornithine | 2.86 | 2.54 | 1.13 | — |
| valine | 1.82 | 1.29 | 1.42 | 1.7 |
| phenylalanine | 3.86 | 1.93 | 2.00 | 4.2 |
| tryptophane | 9.04 | 2.93 | 3.09 | 7.1 |

The terms k', α and Rs are defined as follows:

capacity factor (k') =

[(retention time of antipode) − (dead time)] / (dead time)

separation factor (α) = (volume ratio of antipode adsorbed more strongly) / (volume ratio of antipode adsorbed less strongly)

resolution factor (Rs) =

2 × (distance between a peak of more strongly adsorbed antipode and that of less strongly adsorbed antipode) / (total band width of both peaks)

COMPARATIVE EXAMPLE 1

Amino acids were optically resolved under the same conditions as in Example 1 using a column filled with a silica gel having a copper carboxylate of the following formula as the modifying group. The capacity factor of phenylalanine K'$_L$ and k'$_D$ were 28.8 and 13.9, respectively. The capacity factor of tryptophane k'$_L$ and k'$_D$ were as high as 74.8 and 23.8, respectively, which were practically undesirable. When the flow rate of the solvent was increased to 5 ml/min so as to reduce the time, the pressure applied to the packing was elevated to 90 kg/cm$^2$G and the silica gel was crushed in the continuous operation.

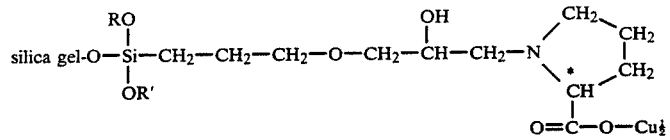

wherein both or either of R and R' represents a methyl group or both or either of them is the same silica gel as above.

SYNTHESIS EXAMPLE 2

A silica gel was dried by heating to 120° to 150° C. in a dry nitrogen stream for 2 to 10 h. 20 g of the dry silica gel was suspended in 100 ml of anhydrous benzene. 8 g of 2-(3,4-epoxycyclohexylethyl)trimethoxysilane was added to the suspension and the mixture was heated under reflux in a dry nitrogen stream. The reaction was carried out for 5 to 10 h while methanol thus formed was removed from the reaction system. After completion of the reaction, the mixture was cooled to room temperature and filtered through a glass filter. The resulting modified silica gel was washed with anhydrous benzene and dried at 40° C. in a vacuum.

6.2 g (0.03 mol) of L-proline benzyl ester dried in a vacuum was added to 250 ml of anhydrous dimethylformamide and the mixture was stirred at 90° C. to obtain a solution. 20 g of the modified silica gel obtained as above was added to this solution and the mixture was agitated at 90° C. for 4 h. The mixture was then cooled to room temperature. 1.9 g (0.033 mol) of sodium hydrosulfide dissolved in anhydrous methanol was added thereto and the mixture was agitated at room temperature for 19 h to convert the benzyl ester group into sodium thiocarboxylate. The obtained, modified silica gel was filtered through a glass filter. The filter cake was washed with methanol to remove excessive sodium L-prolinethiocarboxylate and then it was added to a solution of 12 g of copper sulfate in 100 ml of pure water to obtain the corresponding copper salt.

The structural formula of the product was estimated to be as follows:

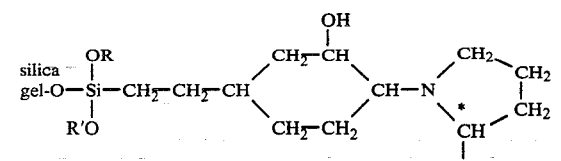

and

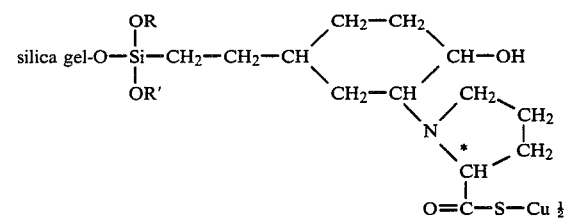

wherein both or either of R and R' represents a methyl group or both or either of them is the same silica gel as above.

EXAMPLE 2

The packing obtained from wholly porous silica gel having an average particle diameter of 10 μm and an average pore diameter of 100 Å in the above Synthesis Example 2 was placed in a stainless steel high-performance liquid chromatographic column (25 cm×0.46 cm). Racemic amino acids were optically resolved at a flow rate of 2 ml/min at 50° C., using a $2.5 \times 10^{-4}$M aqueous copper nitrate solution as the solvent to obtain excellent resolution effects as shown in Table 2. The pressure applied to the packing was 32 kg/cm²G.

TABLE 2

| Amino acid | Capacity factor $k'_L$ | $k'_D$ | Separation factor (α) | Resolution factor (Rs) |
|---|---|---|---|---|
| threonine | 5.00 | 4.00 | 1.25 | 1.67 |
| serine | 5.00 | 3.83 | 1.30 | 1.91 |
| proline | 5.06 | 6.94 | 1.37 | 1.42 |
| histidine | 7.89 | 6.22 | 1.27 | 1.07 |
| isoleucine | 8.56 | 6.28 | 1.36 | 1.71 |
| methionine | 7.67 | 6.83 | 1.12 | 0.65 |
| lysine.HCl | 13.1 | 11.8 | 1.10 | 0.94 |
| ornithine | 12.9 | 11.6 | 1.11 | 0.85 |
| valine | 4.72 | 3.67 | 1.29 | 1.58 |
| phenylalanine | 10.8 | 6.17 | 1.76 | 2.27 |
| tryptophane | 40.5 | 16.8 | 2.41 | 4.44 |

SYNTHESIS EXAMPLE 3

A silica gel was dried by heating to 120° to 150° C. in a dry nitrogen stream for 2 to 10 h. 20 g of the dry silica gel was suspended in 100 ml of anhydrous benzene. 8 g of trimethoxy[2-(7-oxabicyclo[4.1.0]hept-3-yl)ethyl]silane was added to the suspension and the mixture was heated under reflux in a dry nitrogen stream. The reaction was carried out for 5 to 10 h while methanol thus formed was removed from the reaction system. After completion of the reaction, the mixture was cooled to room temperature and filtered through a glass filter. The resulting modified silica gel was washed with anhydrous benzene and dried at 40° C. in a vacuum. 5.6 g of sodium salt of L-proline was dissovled in 250 ml of anhydrous dimethylformamide at 90° C. About 20 g of the above-mentioned silica gel containing 2-(3,4-epoxycyclohexylethyl)silyl group was added to this solution to obtain a suspension, which was agitated at 90° C. for 4 h. The suspension was cooled to room temperature and the resulting modified silica gel was filtered, washed with methanol and added to a solution of 12 g of copper sulfate in 100 ml of pure water to obtain a copper salt. This salt was filtered again and washed with pure water to obtain silica gel chemically bonded with the copper salt of L-proline.

The structural formula of the product was estimated to be as follows:

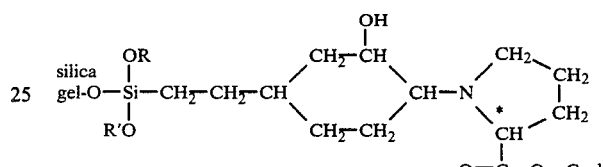

and

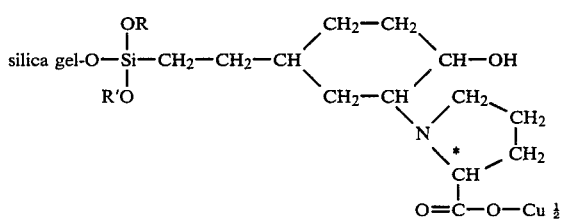

wherein both or either of R and R' represents a methyl group or both or either of them is the same silica gel as above.

EXAMPLE 3

The packing obtained from wholly porous silica gel having an average particle diameter of 10 μm and an average pore diameter of 100 Å in the above Synthesis Example 3 was placed in a stainless steel high-performance liquid chromatographic column (10 cm×0.46 cm).

Racemic amino acids were optically resolved at a flow rate of 2 ml/min at 50° C. using a $5 \times 10^{-4}$M aqueous copper nitrate solution as the solvent to obtain excellent resolution effects as shown in Table 3.

TABLE 3

| Amino acid | Capacity factor $k'_L$ | $k'_D$ | Separation factor (α) | Resolution factor (Rs) |
|---|---|---|---|---|
| threonine | 9.00 | 6.00 | 1.50 | 1.41 |
| serine | 10.3 | 6.75 | 1.52 | 1.56 |
| proline | 7.25 | 12.4 | 1.71 | 1.28 |
| histidine | 12.6 | 7.50 | 1.68 | 1.14 |
| isoleucine | 12.5 | 7.50 | 1.67 | 1.74 |
| methionine | 12.5 | 10.3 | 1.22 | 0.62 |
| valine | 14.4 | 9.00 | 1.60 | 1.59 |
| phenylalanine | 32.4 | 13.6 | 2.38 | 2.56 |
| tryptophane | 111.5 | 32.5 | 3.43 | 4.13 |

SYNTHESIS EXAMPLE 4

A silica gel was dried by heating to 120° to 150° C. in a dry nitrogen stream for 2 to 10 h. 20 g of the dry silica gel was suspended in 100 ml of anhydrous benzene. 6 g of glycidoxypropyltrimethoxysilane was added to the suspension and the mixture was heated under reflux in a dry nitrogen stream. The reaction was carried out for 5 to 10 h while methanol thus formed was removed from the reaction system. After completion of the reaction, the mixture was cooled to room temperature and filtered through a glass filter. The resulting modified silica gel was washed with anhydrous benzene and dried at 40° C. in vacuum. 1.88 g of disodium salt of L-N-octyl-hydroxyproline was dissolved in 50 ml of anhydrous dimethylformamide. 4 g of the above obtained silica gel containing a glycidoxypropylsilyl group was suspended in said solution. The suspension was agitated at 90° C. for 6 h.

The modified silica gel was filtered, washed with methanol and added to a solution of 6 g of copper sulfate in 50 ml of pure water to obtain a corresponding copper salt. This salt was filtered again and washed with pure water to obtain silica gel chemically bonded with copper L-N-ocyl-2-pyrrolidinecarboxylate.

The structural formula of the product was estimated to be as follows:

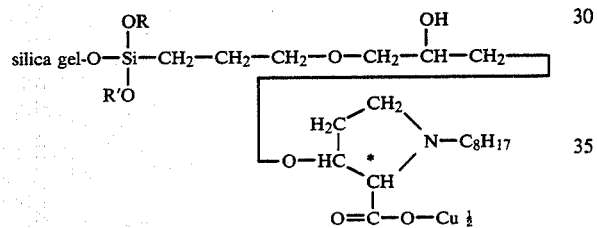

wherein both or either of R and R' represents a methyl group or both or either of them is the same silica gel as above.

EXAMPLE 4

Various racemic amino acids were optically resolved with the packing obtained in Synthesis Example 4. The packing obtained from wholly porous silica gel having an average particle diameter of 10 μm and an average pore diameter of 100 Å in the above Synthesis Example 1 was placed in a stainless steel high-performance liquid chromatographic column (25 cm×0.46 cm). Racemic amino acids were optically resolved at a flow rate of 3 ml/min at 50° C. using a $5\times10^{-4}$M aqueous copper nitrate solution as the solvent to obtain excellent resolution effects shown in Table 4.

TABLE 4

| Amino acid | Capacity factor $k'_L$ | Capacity factor $k'_D$ | Separation factor ($\alpha$) | Resolution factor (Rs) |
|---|---|---|---|---|
| threonine | 6.56 | 4.89 | 1.34 | 1.7 |
| serine | 6.22 | 4.56 | 1.37 | 1.6 |
| proline | 5.78 | 10.3 | 1.79 | 3.1 |
| histidine | 16.3 | 11.0 | 1.48 | 1.7 |
| isoleucine | 8.44 | 7.78 | 1.09 | — |
| leucine | 8.33 | 7.56 | 1.10 | — |
| valine | 7.56 | 6.56 | 1.15 | 0.66 |
| phenylalanine | 18.8 | 9.22 | 2.04 | 3.9 |
| tryptophane | 61.3 | 15.9 | 3.86 | 6.6 |

SYNTHESIS EXAMPLE 5

A silica gel was dried by heating to 120° to 150° C. in dry nitrogen stream for 3.5 h. 50 g of the dry silica gel was suspended in 300 ml of anhydrous benzene. 20 ml of glycidoxypropyltrimethoxysilane was added to the suspension and the mixture was heated under reflux in dry nitrogen stream. The reaction was carried out for 16 h while methanol thus formed was removed from the reaction system. After completion of the reaction, the mixture was cooled to room temperature and filtered through a glass filter. The resulting modified silica gel was washed with anhydrous benzene and dried at 40° C. in a vacuum. 3.0 g of an adduct obtained by reacting sodium salt of L-proline with cyclohexane epoxide was dissolved in 50 ml of anhydrous dimethylformamide. 3.5 g of the above obtained silica gel containing glycidoxypropylsilyl group was suspended in said solution. The suspension was agitated at 90° C. for 15 h.

The modified silica gel was filtered, washed with methanol and added to a solution of 2 g of copper sulfate in 50 ml of pure water to obtain a corresponding copper salt. This salt was filtered again and washed with pure water to obtain silica gel chemically bonded with a copper salt of N-substituted L-proline.

The structural formula of the product was estimated to be as follows:

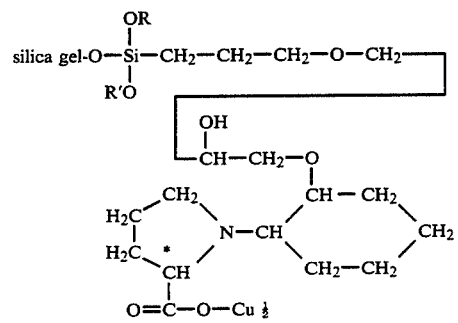

wherein both or either of R and R' represents a methyl group or both or either of them is the same silica gel as above.

EXAMPLE 5

Various racemic amino acids were optically resolved with the packing obtained in Synthesis Example 5. The packing obtained from wholly porous silica gel having an average particle diameter of 10 μm and an average pore diameter of 60 Å in the above Synthesis Example 1 was placed in a stainless steel high-performance liquid chromatographic column (25 cm×0.46 cm). Racemic amino acids were optically resolved at a flow rate of 2 ml/min at 50° C. using a $5\times10^{-4}$M aqueous copper nitrate solution as the solvent to obtain excellent resolution effects as shown in Table 5.

TABLE 5

| Amino acid | Capacity factor $k'_L$ | Capacity factor $k'_D$ | Separation factor $\alpha$ |
|---|---|---|---|
| valine | 14.8 | 10.3 | 1.44 |
| methionine | 14.8 | 13.0 | 1.11 |
| phenylalanine | 34.3 | 16.9 | 2.03 |
| serine | 11.4 | 7.7 | 1.48 |
| proline | 8.6 | 13.9 | 0.62 |
| threonine | 11.9 | 8.5 | 1.40 |
| histidine | 16.1 | 9.7 | 1.66 |
| isoleucine | 17.0 | 11.7 | 1.45 |

TABLE 5-continued

| Amino acid | Capacity factor $k'_L$ | Capacity factor $k'_D$ | Separation factor $\alpha$ |
|---|---|---|---|
| tryptophane | 80.9 | 25.5 | 3.17 |

SYNTHESIS EXAMPLE 6

Silica gel was heated to 120° to 150° C. in dry nitrogen stream for 2 h and then heated in vacuum for 4 h. 50 g of the dried silica gel was suspended in 300 ml of anhydrous benzene. 25 ml of glycidoxypropyltrimethoxysilane was added to the suspension and the mixture was heated under reflux in a dry nitrogen stream. The reaction was carried out for 8 h while methanol thus formed was removed from the reaction system. After completion of the reaction, the mixture was cooled to room temperature and filtered through a glass filter. The resulting modified silica gel was washed with anhydrous benzene and dried at 40° C. in vacuum. An adduct obtained by reacting 1.5 g of sodium salt of L-proline with 5.0 g of a straignt-chain α-olefin epoxide having 15 to 18 carbon atoms was dissolved in 10 ml of anhydrous dimethylformamide. 6 g of the above obtained silica gel containing glycidoxypropylsilyl group was suspended in said solution. The suspension was agitated at 90° C. for 15 h.

The modified silica gel was filtered, washed with methanol and added to a solution of 1 g of copper sulfate in 50 ml of pure water to obtain a corresponding copper salt. This salt was filtered again and washed with pure water to obtain silica gel chemically bonded with a copper salt of N-substituted L-poline.

The structural formula of the product was estimated to be as follows:

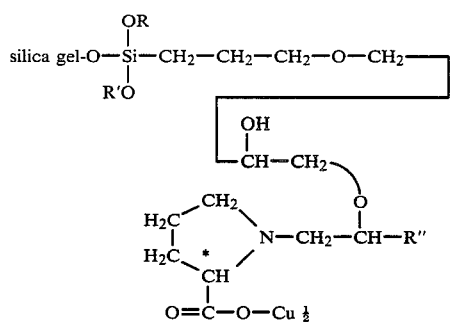

wherein both or either of R and R' represents a methyl group or both or either of them is the same silica gel as above and R" represents a straight-chain alkyl group having 13 to 16 carbon atoms.

EXAMPLE 6

Various racemic amino acids were optically resolved with the packing obtained in Synthesis Example 6. The packing obtained from wholly porous silica gel having an average particle diameter of 10 μm and an average pore diameter of 60 Å in the above Synthesis Example 5 was placed in a stainless steel high-performance liquid chromatographic column (25 cm×0.46 cm). Racemic amino acids were optically resolved at a flow rate of 2 ml/min at 50° C. using a $5\times10^{-4}$M aqueous copper nitrate solution as the solvent to obtain excellent resolution effects similar to those obtained in Example 5.

What is claimed is:

1. A packing for use in the optical resolution of racemic compounds, comprising a substance of the general formula (I):

wherein at least one of $Y^1$, $Y^2$ and $Y^3$ represents a silica gel and siloxane bond with the silica gel and the balance is selected from the group consisting of a hydrogen atom, an alkyl group having 1 to 20 carbon atoms, an aryl group having 6 to 20 carbon atoms, an aralkyl group having 7 to 20 carbon atoms, a halogen atom, a hydroxy group, and an alkoxy group having 1 to 20 carbon atoms, and W represents $$-X-R \qquad (1)$$

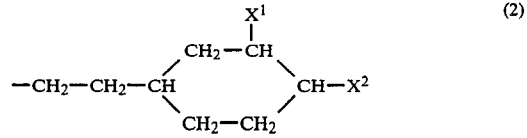

$$-X-R^1 \text{ or} \qquad (3)$$
$$-X-R^2 \qquad (4)$$

in which X represents a divalent group having 1 to 30 carbon atoms,

R represents an optically active group of the general formula:

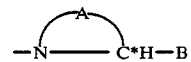

where A is a substituted or unsubstituted alkylene group having 2 or 3 carbon atoms and B is a metal thiocarboxylate group, one of $X^1$ and $X^2$ represents a hydroxy group and the other represents an optically active group of the formula:

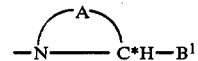

where $B^1$ is a metal carboxylate group,
$R^1$ represents an optically active group of the general formula:

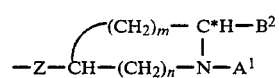

where m and n are each 0 or an integer of 1 to 3 and the total of these numbers is up to 3, $B^2$ is a copper carboxylate or thiocarboxylate, Z is an oxygen atom, a sulfur atom or an amino group and $A^1$ is a hydrogen atom, an alkyl group having 1 to 40 carbon atoms, an aryl group having 6 to 40 carbon atoms, an aralkyl group having 7 to 47 carbon atoms or a group having 1 to 40 carbon atoms and a hetero atom, and $R^2$ represents an optically active group of the general formula:

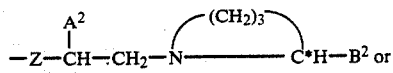

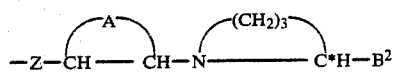

where $A^2$ is a hydrogen atom, an alkyl group having 1 to 40 carbon atoms, an aryl group having 6 to 40 carbon atoms, an aralkyl group having 7 to 47 carbon atoms or a group having 1 to 40 carbon atoms and a hetero atom, $A^3$ is alkylene having 2 to 6 carbon atoms and refers to an asymmetric carbon atom.

2. A packing for use in the optical resolution of racemic compounds according to claim 1 wherein W in the general formula (I) is:

$$-X-R. \quad (1)$$

3. A packing for use in the optical resolution of racemic compounds according to claim 1 wherein W in the general formula (I) is:

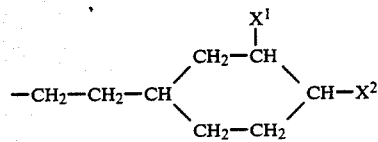

4. A packing for use in the optical resolution of racemic compounds according to claim 1 wherein W in the general formula (I) is:

$$-X-R^1. \quad (3)$$

5. A packing for use in the optical resolution of racemic compounds according to claim 1, wherein W in the general formula (I) is:

$$-X-R^2. \quad (4)$$

6. A packing as claimed in claim 1 in which said silica gel has a particle diameter of 0.1 to 1000 μm and a pore diameter of 10 to 10000 Å.

7. A packing as claimed in claim 1 in which X is a divalent alkylene or arylene group which may optionally contain a hetero atom therein.

8. A packing as claimed in claim 1 in which X is $-CH_2-$, $-CH_2CH_2CH_2-$, $-CH_2CH_2-$,

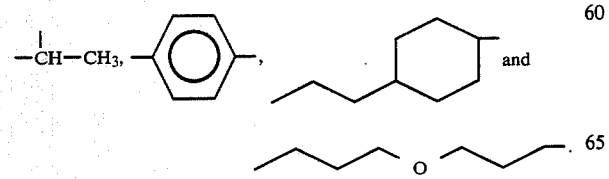

9. A packing as claimed in claim 2 in which

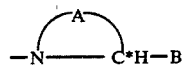

is a metal thiocarboxylate of an optically acitve D- or L-compound selected from the group consisting of 2-azetidinecarboxylic acid, proline, hydroxyproline and allohydroxyproline.

10. A packing as claimed in claim 9 in which said compound is an L-compound.

11. A packing as claimed in claim 2 in which

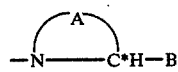

is

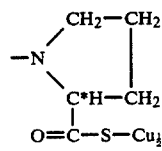

12. A packing as claimed in claim 3, in which

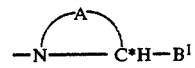

is a metal carboxylate of an optically active, D- or L-compound selected from the group consisting of 2-azetidinecarboxylic acid, proline, hydroxyproline and allohydroxyproline.

13. A packing as claimed in claim 12 in which said compound is an L-compound.

14. A packing as claimed in claim 3 in which

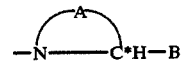

is

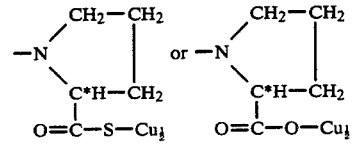

15. A packing as claimed in claim 4 in which

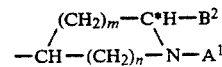

is a copper carboxylate or thiocarboxylate of optically active D- or L-hydroxyproline or allohydroxyproline substituted with substituent $A^1$.

16. A packing as claimed in claim 4 in which

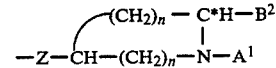

is

-continued
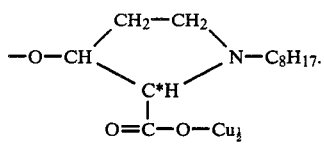
17. A packing as claimed in claim 5 in which $R^2$ is
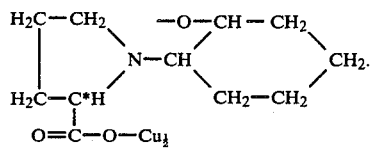
18. A packing as claimed in claim 5 in which $R^2$ is
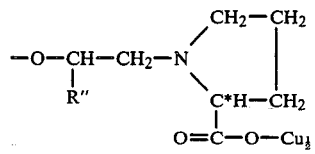
wherein R'' is straight chain alkyl having 13 to 16 carbon atoms.
* * * * *